US00PP33355P3

(12) United States Plant Patent
Green et al.

(10) Patent No.: US PP33,355 P3
(45) Date of Patent: Aug. 17, 2021

(54) AVOCADO TREE NAMED 'SHSR-04'

(50) Latin Name: ***Persea americanan* Mill.**
Varietal Denomination: SHSR-04

(71) Applicants: George Hulme Green, South Kolan (AU); Sunshine Horticultural Services Pty Ltd, Woodgate (AU); Horticulture Innovation Australia Limited, Sydney (AU)

(72) Inventors: George Hulme Green, South Kolan (AU); Anthony William Whiley, Woodgate (AU)

(73) Assignees: HORTICULTURE INNOVATION AUSTRALIA LIMITED, New South Wales (AU); SUNSHINE HORTICULTURAL SERVICES PTY LTD, Queensland (AU)

( * ) Notice: Subject to any disclaimer, the term of this patent is extended or adjusted under 35 U.S.C. 154(b) by 0 days.

(21) Appl. No.: 16/909,121

(22) Filed: Jun. 23, 2020

(65) Prior Publication Data

US 2020/0404821 P1 Dec. 24, 2020

(30) Foreign Application Priority Data

Jun. 24, 2019 (AU) ..... PBR 2019/129

(51) Int. Cl.
*A01H 6/52* (2018.01)
*A01H 5/00* (2018.01)

(52) U.S. Cl.
USPC ..... Plt./200
CPC ..... *A01H 6/525* (2018.05)

(58) Field of Classification Search
USPC ..... Plt./200
See application file for complete search history.

(56) References Cited

PUBLICATIONS

Proceedings VII World Avocado Congress 2011 (Aetas VII Congress Mundial del Aguacate 2011) Cairns Australia Sep. 5-9, 2011.*
A.W. Whiley et al. Rootstock improvement for the Australian Avocado Industry Phase IV 2013.*

* cited by examiner

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct cultivar of Avocado tree named 'SHSR-04' is disclosed. The new variety is characterized by forming greyed-purple colored young leaves, providing ovoid shaped fruit which is rounded at the stalk end, and exhibiting high resistance to *Phytophthora* root rot. The new variety is particularly well suited for use as rootstock for grafting other avocado cultivars, including 'Hass'.

4 Drawing Sheets

CROSS-REFERENCE TO RELATED APPLICATIONS

This application claims priority to Plant Breeders' Right Application Number 2019/129, which was filed in Australia and was received on Jun. 24, 2019 and accepted on Aug. 27, 2019, the contents of which are hereby incorporated by reference for all purposes.

Latin name of genus and species of plant claimed: *Persea americanan* Mill.

Variety denomination: 'SHSR-04'.

BACKGROUND OF THE INVENTION

The present invention relates to a new and distinct cultivar of Avocado tree botanically known as *Persea americanan* Mill. and herein referred to by the cultivar name 'SHSR-04'. The new variety displays high resistance to *Phytophthora* root rot, which is a debilitating disease of Avocado trees worldwide.

The new variety was discovered in a cultivated area at South Kolan, Queensland, Australia. The new variety was discovered in October 2003 in an avocado orchard heavily infested with root rot, caused by *Phytophthora cinnamomi*

Rands, at South Kolan, Queensland, Australia. Most trees in the orchard died of root rot, however, the new variety was the only survivor that carried fruit and maintained excellent commercial health. The new variety originated from a 'Hass' avocado tree, grafted to a seedling rootstock belonging to the Guatemalan horticultural race. The variety of the parent seedling rootstock is unknown.

Genetic material from the new variety seedling rootstock was recovered by pruning the tree back below the graft union, then taking several bud-bearing sticks from new growth made by the new variety.

Several asexual reproductions of the seedling rootstock were made in from November 2005 to February 2006 at Nambour, Queensland, Australia by grafting the recovered bud-sticks to seedling rootstocks.

Grafted bud-sticks were subsequently rooted following standard procedures for producing clonal avocado rootstocks known in the art. The new variety was grafted with 'Hass' (U.S. Plant Pat. No. 139, now expired) in the nursery and planted in field trials that include 'Merensky 1' (known as 'Latas' in Australia) (U.S. Plant Pat. No. 17,947); 'Merensky 2' (known as 'Dusa' in Australia) (U.S. Plant Pat. No. 15,309) that were also clonally rooted and grafted with the 'Hass' cultivar. 'Hass' trees grafted to the asexually reproduced new variety always showed the same superior resistance to *Phytophthora* root rot as the original tree and had superior root rot resistance compared to trees grafted to other rootstocks in the field trials.

In addition, field observations indicate that, when grafted with 'Hass', the new variety consistently yields higher than 'Merensky 2' rootstocks grafted to 'Hass'.

Thus, asexual propagation techniques, as described above, in Queensland, Australia, have demonstrated that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

The following characteristics of the new cultivar have been repeatedly observed and can be used to distinguish 'SHSR-04' as a new and distinct cultivar of avocado plant:

(a) forms greyed-purple colored young leaves, (b) provides ovoid shaped fruit which is rounded at the stalk end, and (c) exhibits high resistance to *Phytophthora cinnamomi* root rot.

The new variety of the present invention can readily be distinguished from its ancestors. Although the parental cultivars of the new variety are unknown, all known Guatemalan horticultural race cultivars display reduced resistance to root rot compared to the new variety. To date, all identified *Phytophthora* root rot resistance rootstocks are of Mexican horticulture race origin. Accordingly, the new variety is the first known Guatemalan horticultural race origin plant that provides *Phytophthora* root rot resistance rootstock. In addition, seeds from the new variety were sown and 200 seedlings from the new variety seeds all had much lower resistance to *Phytophthora* root rot compared to the new variety. Moreover, the new variety can be readily distinguished from other similar non-parental varieties. For example, Table 1 indicates distinguishing characteristics of the new variety from 'Merensky 1' and 'Merensky 2', as observed under the same conditions.

TABLE 1

| Characteristic | 'SHSR-04' | 'Merensky 1' | 'Merensky 2' |
|---|---|---|---|
| Color of young leaf | Greyed-purple | Yellow-green | Yellow-green |
| Resistance to anthracnose (*Colletotrichum gloeospotiodes* Penz.) | High resistance | Moderate to high resistance | Highly susceptible |
| Shape of fruit | Ovoid and rounded at stalk end | Pyriform and narrowly rounded at the stalk end | Pyriform and narrowly rounded at the stalk end |
| Flower Type | A group | B group | B group |
| Style shape | Kinked | Slightly curved | Slightly curved |

No commercial sales of the new variety have occurred at the time of filing the instant application.

BRIEF DESCRIPTION OF THE PHOTOGRAPHS

The accompanying photographs show, as nearly true as it is reasonably possible to make the same in color illustrations of this type, typical specimens of the new variety.

DETAILED BOTANICAL DESCRIPTION

Figure 1:
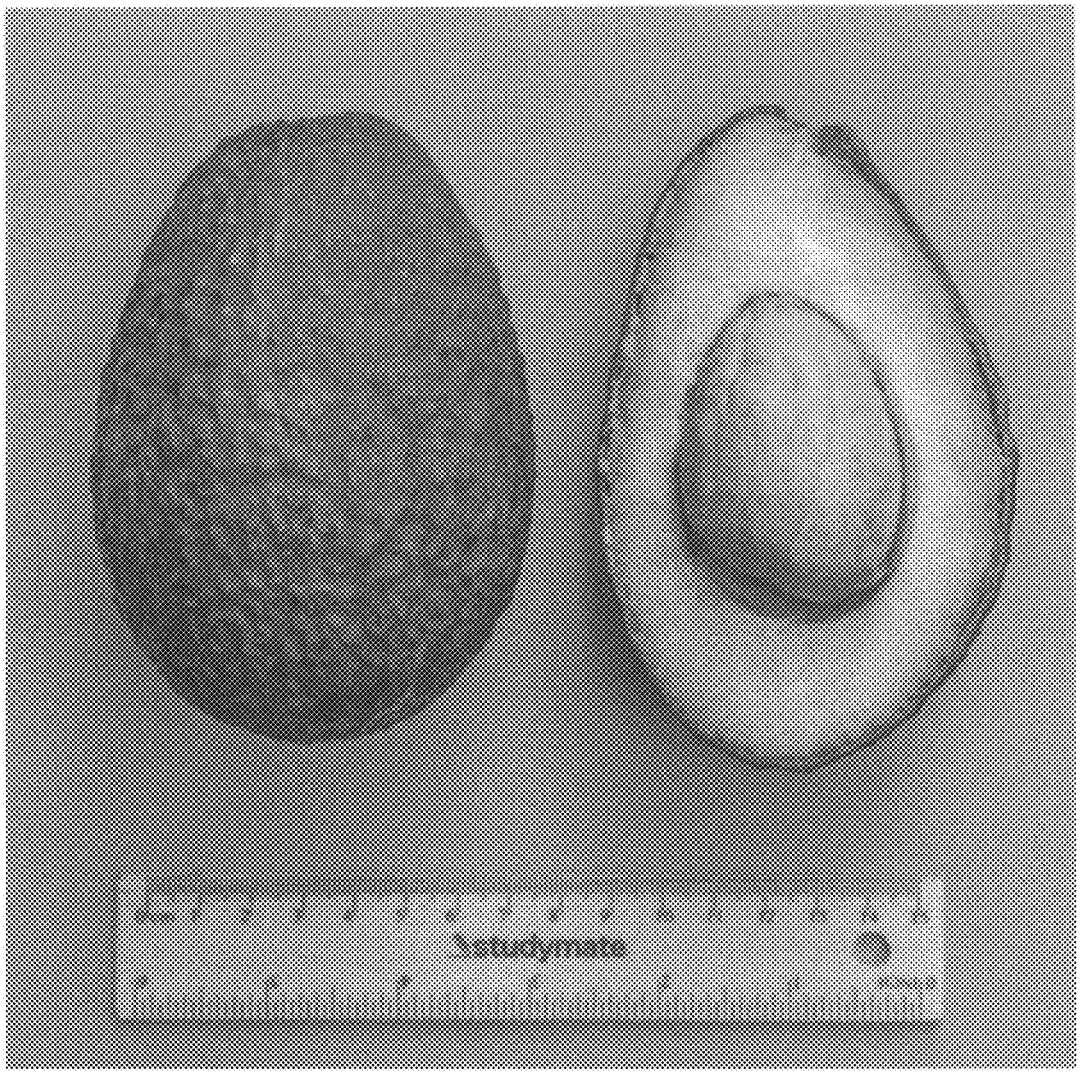
FIG. 1 illustrates a specimen of mature fruit—cross section, skin, and seed.
Figure 2:
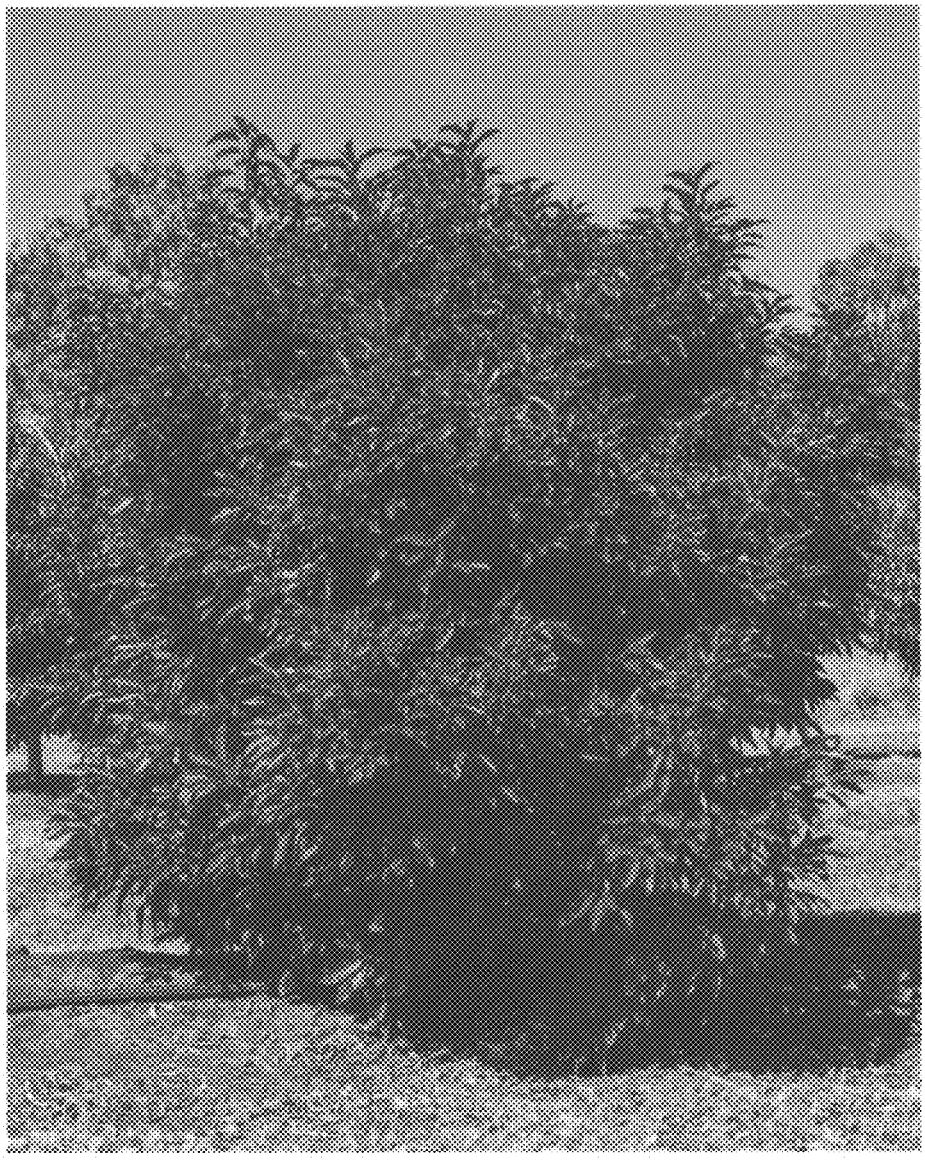
FIG. 2 illustrates a specimen of the tree—3 years old.
Figure 3:
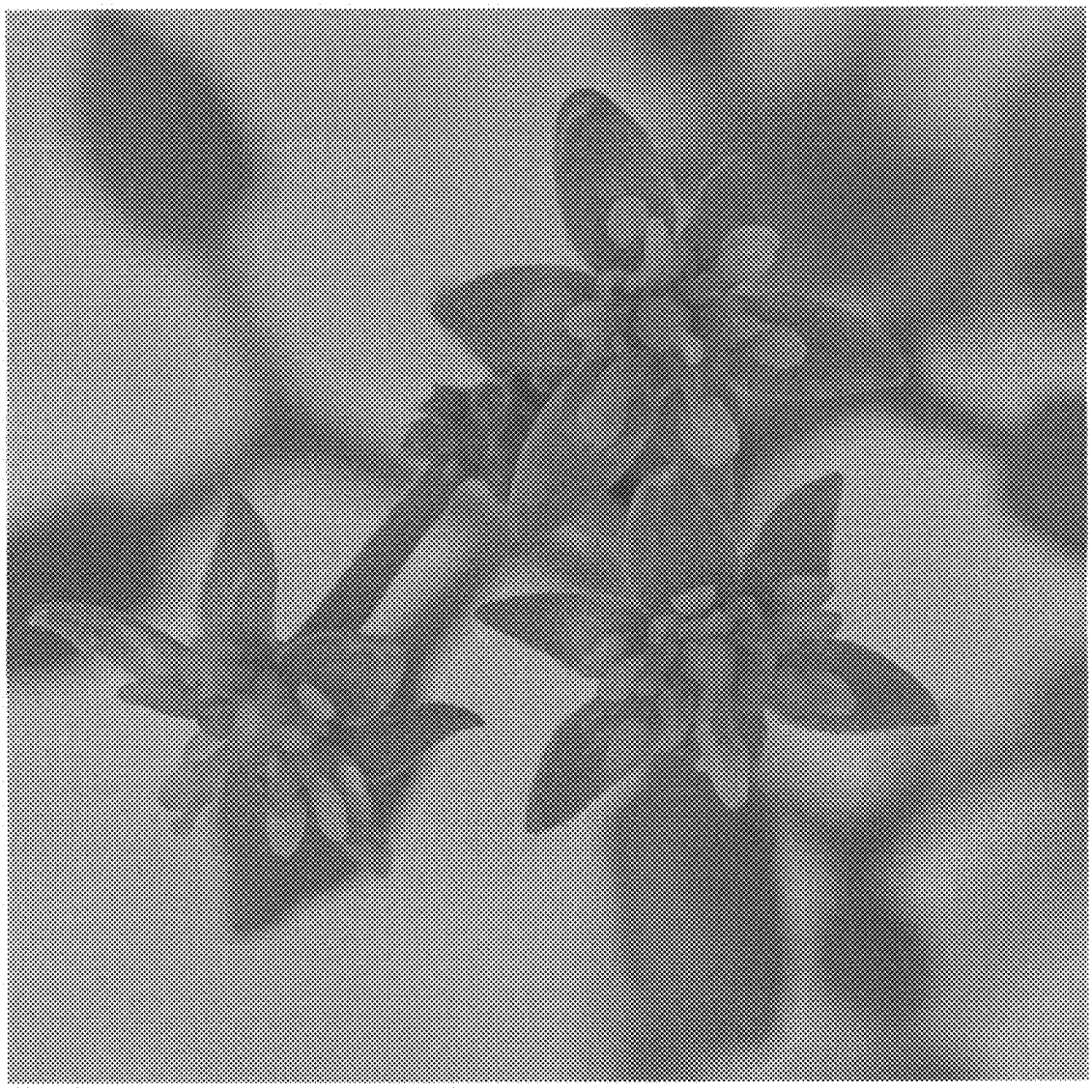
FIG. 3 illustrates a specimen of flowers—female opening.
Figure 4:
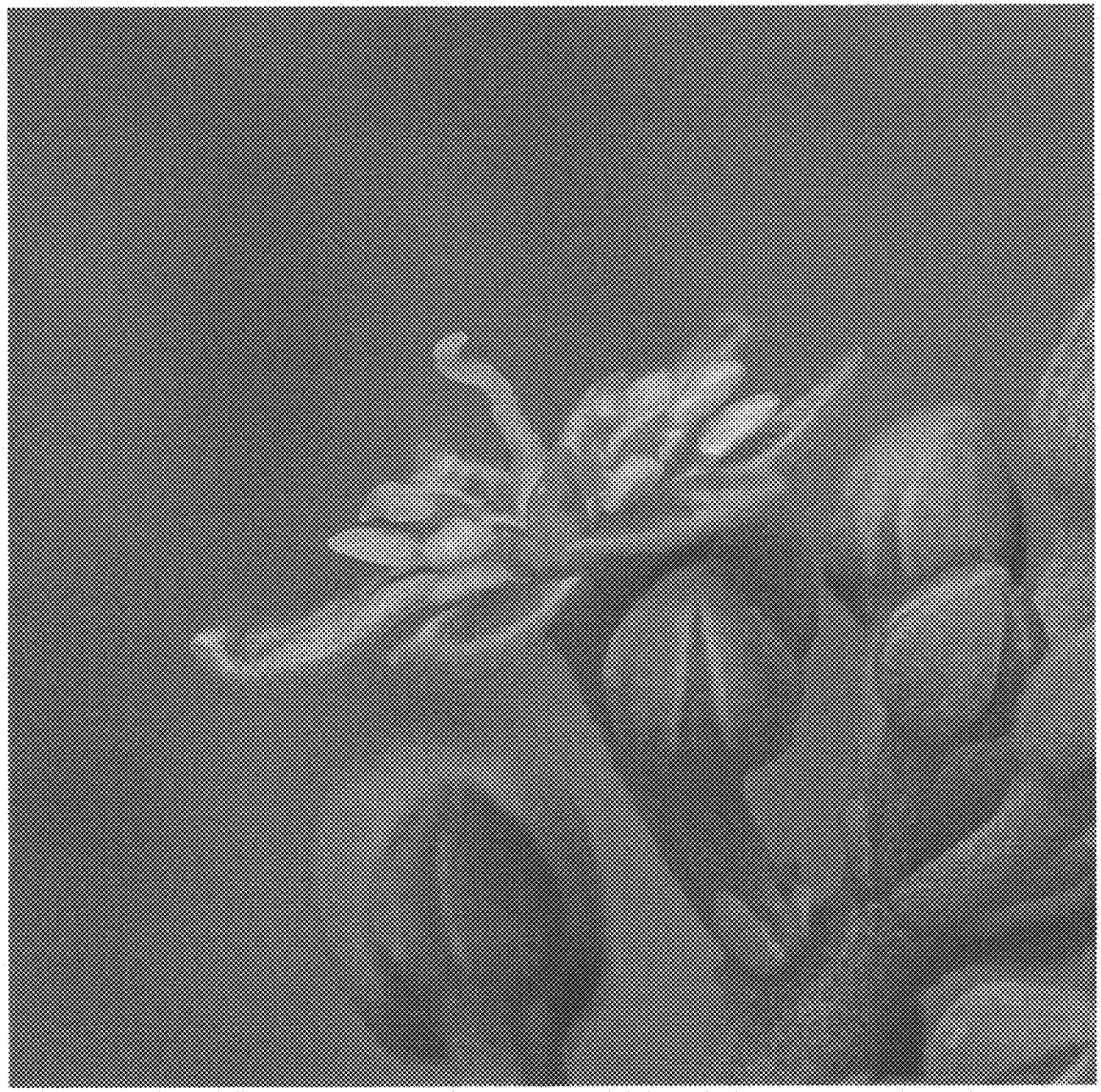
FIG. 4 illustrates a single flower—side view—showing kinked style shape.

The chart used in the identification of colors described herein is that of The Royal Horticultural Society (R.H.S. Colour Chart), London, England, 1995, 3rd Edition, except where general color terms of ordinary significance are used. The terminology which precedes reference to the chart has been added to indicate the corresponding color in more common terms.

The description is based on specimens of the new variety in Australia, grown in the vicinity of Walkamin (latitude 17.12 S, longitude 145.42 E, altitude 496 m), Queensland, Australia. The mean annual maximum/minimum temperatures at this site are 27.4/17.1° C. and the mean annual rainfall 1013.8 mm according to the Australian Bureau of Meteorology 1968-2020.

Scions of the new variety were top-worked to seedlings of 'Velvick' avocado (not patented) and 10 single tree replicates of each cultivar were planted at 10×6 m intervals following a completely randomised design. The soil type is a red clay-loam derived from basalt, deep, well-structured and porous with high natural fertility and an acid-neutral pH in the A horizon and strongly acidic (5.5 pH) in the B horizon, as known to one skilled in the art. Commonly defined a krasnozem the soil has a clay content of about 60% with medium water-holding capacity. The orchard site was recently cleared from native trees and had never been cropped at the time trees were planted, hence was free of *Phytophthora cinnamomi* (avocado root rot). Nutrition requirements were based on annual leaf analyses with fertilizers applied through fertigation. Soil moisture was monitored by Environscan® probes and irrigation applied by under-tree sprinklers maintaining ≥80% of field capacity in the drip zone. Pest and disease treatments were applied as required.

For the botanical characteristics measured, 20 random measurements were taken from each tree replicate. The descriptions herewith were made from 3-4 year-old trees that had commenced cropping.

Botanical classification: *Persea americana* Mill cultivar SHSR-04.

Tree description:

*Growth habit.*—Medium vigor, medium size, with a semi-upright growth habit.

*Wood of one-year old branch.*—Color: commonly near yellow-green (RHS 147B). — texture: smooth bark, having inconspicuous lenticels.

*Main stem.*—Color of the trunk: commonly near grey-brown (RHS 199B). — bark texture: corky.

*Young shoot.*—Color on new autumn growth (approximately 4 weeks old): commonly near yellow-green (RHS 146C). — anthocyanin intensity: medium.

*Lenticels.*—Measured on new autumn growth: strong conspicuousness of lenticels, color is commonly near greyed/red (RHS 181A), and density of approximately 20/cm$^2$.

Foliage description:

*Young leaf.*—Upper side: color is commonly near greyed-purple (RHS 183B) with medium/high glossiness. — under side: color is commonly near greyed-purple (RHS 183D).

*Mature leaf.*—Mean length: 15.5 cm. — mean width: 6.1 cm. — leaf shape: lanceolate. — glossiness of the upper surface: moderate. — color of upper surface: commonly near yellow-green (RHS 147A). — color of lower surface: commonly near green (RHS 138A). — prominence of veins on the lower surface: moderate in relief. — vein color: commonly near yellow-green (RHS) 152C). — shape: cross-sectional shape is slightly curved upwards, reflexing of the apex of mature leaves is absent. — anise aroma: no presence.

*Petiole.*—Mean length: 4.0 cm. — color: commonly near yellow-green (RHS 146C).

Fruit:

*Quality.*—High resistance to anthracnose (*Colletotrichum gloeospotiodes* Penz.) and at maturity, excellent eating quality with an oil-rich flesh, and nutty-flavor.

*Shape.*—Ovoid and rounded at the stalk end. — stylar region: moderately flattened.

*Size of mature fruit.*—Mean length: 12.3 cm. — mean diameter: 7.7 cm. — length/diameter ratio: 1.60.

*Skin color when ripe.*—Commonly near green (RHS 135A) skin color.

*Skin texture.*—Pebbly.

*Longitudinal ridges.*—Absent.

*Skin thickness.*—Medium/thick with weak adherence to the flesh.

*Flesh color.*—Commonly near yellow-green (RHS 150C) with the color of flesh close to the skin commonly near green (RHS 141C).

*Seed.*—Mean seed weight: 63 g. — shape (in longitudinal section): ovate. — color of a fresh seed coat from a ripe fruit: commonly near brown (RHS 200B).

*Pedicel.*—The pedicel is thicker than the respective attached peduncles and the "nail-head" shaped pedicel is absent.

*Harvest.*—In Australia, fruit matures in mid-late May; the mean flesh recovery is 82.0%.

Flowers:

*Flowering time.*—Begins flowering in the third week of August reaching a peak in the second week of September with flowering completed by the last week of September.

*Type.*—A unique behaviour described as 'protogynous dichogamy with synchronous daily complementarity' common to all avocado cultivars, as known in the art.

*Flower.*—Flower Type A group: the flower opens first in the morning as female (stigma receptive) closing around midday, then reopens the afternoon of the following day as male (pollen shedding).

*Floral structures.*—Flowers are borne in thyrses, that are a compact branching inflorescence in which the central axis is indeterminate and lateral axes are determinate. The central axis of thyrses are short.

*Bud size.*—Not observed.

*Bud shape.*—Not observed.

*Bud color.*—Not observed.

*Petals.*—Three elements in each of two perianth whorls, the petals have entire margins and are tomentose on both surfaces. Colors not observed.

*Stamen.*—There commonly are nine fertile stamens with each having two basal orange nectar glands, and three staminodes.

*Pistil.*—Flowers have a single pistil with a slender style and small stigmatic surface and a single ovule at the base; the style of the Invention is kinked.

*Number of flowers/thyrse.*—Not observed.

Plants of the 'SHSR-04' variety have not been observed under all possible environmental conditions to date. Accordingly, it is possible that the phenotypic expression may vary somewhat with changes in light intensity and duration, cultural practices, and other environmental conditions.

DISEASE RESISTANCE DESCRIPTION:

The descriptive pathology information that follows relates to the 'SHSR-04' avocado tree, as well as the comparative cultivars 'Merensky 1' known as Latas in Australia, and 'Merensky 2' (U.S. Plant Pat. No. 15309P3) known as Dusa in Australia, grown as asexually propagated rootstocks grafted with 'Hass' scions, planted in the vicinity of Duranbah (latitude 28.32° S, longitude 153.53° E, altitude 51.5 m), NSW, Australia. The mean annual maximum/minimum temperatures at this site are 25.7/14.5° C. and the mean annual rainfall 1616.3 mm.

Rootstocks were produced using the Ernst micro-cloning technique, as known in the art. "Nurse" seeds were planted in composted pine bark in 90×90 mm pots and grafted 50 mm above the medium surface with scions of the Invention and comparators. Once scions grew, plants were placed in complete darkness at 27±3° C. for 12-15 days, during which time approximately 300 mm of etiolated growth occurred. They were then removed from these conditions and the base of the etiolated shoot treated with 0.8% potassium indole butyric acid. A 50×50×120 mm ribbed tube was slid down over the shoot and filled with composted pine bark and then placed in 30% shade until roots appeared at the bottom of the tube. Once rooted, these shoots were cut from the parent plant, placed in a composted pine bark medium in 5 L poly nursery bags and grown until they were large enough to graft with 'Hass' scions. The trees were further grown to approximately 800 mm tall before field-planting.

The *Phytophthora* root rot (PRR) resistance test was carried out on a site that had previously been cleared of mature avocado trees that were declining due to PRR. Two planting rows were prepared at a distance of 3 m apart. Planting spaces were prepared at 3 m intervals along rows and irrigation installed.

To enable trees to establish in the *Phytophthora* infested field a protection protocol was applied for the first 12 months after planting. The day before planting, each tree was drenched with 1 L of a 0.1% v/v potassium phosphonate solution (Agri-Fos 600®, Agrichem, Australia). At planting, 60 g of metalaxyl-M (Ridomil® Gold 25 G, Syngenta) and 60 g of a commercial general compound fertiliser (CK77, CK Life Sciences International (Holdings) Inc. and Rustica Plus, Campbells Fertiliser Australasia) were applied to the soil around each tree. *Phytophthora* protection measures were imposed during the establishment period so that new trees could begin to grow vigorously to produce a more favorable root:shoot ratio and have the opportunity to express resistance once measures were discontinued. Potassium phosphonate was applied monthly to young trees either as a foliar spray of 0.5% v/v Agri-Fos 600® adjusted to a pH of 7.2 applied to runoff using a backpack spray unit or as a bark application of 20% v/v potassium phosphonate in 2% v/v bark penetrant Pulse® (Nufarm Australia Ltd) applied to the trunk of trees using a paint brush or backpack spray unit to 1 m above ground level. Trees were regularly fertilized throughout the trial and irrigated to maintain good soil moisture.

Ten replicate trees of each rootstock were used in the trial except 'SHSR-04' for which only eight plants were available. Trees were planted in May 2006 in a randomized block design, and the PRR management regime described above was maintained until November 2007.

The effect of PRR on tree health was assessed regularly using a standard tree health scale used in *Phytophthora* research, as known in the art, where 0=vigorous and healthy, to 10=dead. Tree health ratings were obtained 11 times between November 2006 and March 2008. Confirmation of *Phytophthora cinnamomi* in soil and roots of surviving trees, at the completion of the evaluation was established as known in the art.

Statistical analyses of tree health data were conducted using GenStat 11 data analysis software for a randomized block design analysis of variance. Fisher's protected least significant difference (LSD) test (P=0.05) was used for pair-wise comparisons of means.

When evaluated in soils with high levels of *Phytophthora cinnamomi*, 'SHSR-04' was strongly resistant to *Phytophthora* root rot and was significantly (ANOVA; P=0.05) more resistant than 'Merensky 1' and Merensky 2' grown at the Duranbah site. The level of resistance may vary depending on edaphic conditions at other sites.

We claim:

1. A new and distinct Avocado tree characterized by the following combination of characteristics:

(a) forms greyed-purple colored young leaves, (b) provides ovoid shaped fruit which is rounded at the stalk end, and (c) exhibits high resistance to *Phytophthora cinnamomi* root rot;

substantially as herein shown and described.

* * * * *